(12) United States Patent
Phillips et al.

(10) Patent No.: US 9,867,802 B2
(45) Date of Patent: Jan. 16, 2018

(54) **METHOD OF TREATING *SCEDOSPORIUM SPP.* INFECTION**

(71) Applicant: BIODIEM LIMITED, Melbourne, Victoria (AU)

(72) Inventors: Julie Phillips, Denistone (AU); Tania Sorrell, Riverview (AU); Sharon Chen, East Lindfield (AU)

(73) Assignee: BIODIEM LIMITED, Melbourne (AU)

( * ) Notice: Subject to any disclaimer, the term of this patent is extended or adjusted under 35 U.S.C. 154(b) by 0 days.

(21) Appl. No.: 14/404,851

(22) PCT Filed: May 13, 2013

(86) PCT No.: PCT/AU2013/000487
§ 371 (c)(1),
(2) Date: Dec. 1, 2014

(87) PCT Pub. No.: WO2013/177608
PCT Pub. Date: Dec. 5, 2013

(65) Prior Publication Data
US 2015/0126436 A1 May 7, 2015

(30) Foreign Application Priority Data

May 30, 2012 (AU) ................................ 2012902243

(51) Int. Cl.
| | | |
|---|---|---|
| *A61K 31/357* | (2006.01) | |
| *A61K 31/04* | (2006.01) | |
| *A61K 31/36* | (2006.01) | |
| *A61K 45/06* | (2006.01) | |
| *A61K 31/423* | (2006.01) | |
| *A61K 31/4184* | (2006.01) | |

(52) U.S. Cl.
CPC ............ *A61K 31/357* (2013.01); *A61K 31/04* (2013.01); *A61K 31/36* (2013.01); *A61K 31/4184* (2013.01); *A61K 31/423* (2013.01); *A61K 45/06* (2013.01)

(58) Field of Classification Search
None
See application file for complete search history.

(56) References Cited

U.S. PATENT DOCUMENTS

2008/0220103 A1* 9/2008 Birnbaum .............. A01N 25/00
424/735

FOREIGN PATENT DOCUMENTS

| WO | WO02102789 A1 | * 10/2002 |
| WO | WO-2002-102789 A1 | 12/2002 |
| WO | WO 02102789 A1 | * 12/2002 |

OTHER PUBLICATIONS

Cortez, Karoll J. et al, "Infections caused by scedoporium spp." Clin. Microbiol. Rev. (2008) 21(1) p. 157-197.*
Horsfall, J. et al. "Fungitoxicity of Dioxanes, Dioxolanes, and Methylenedioxybenzenes," The Connecticut Agricultural Experiment Station Bulletin 673: 1-44 (Jun. 1965).
Lo, K. et al. "A Study of Fluorinated β-Nitrostyrenes as Antimicrobial Agents," Applied Sciences vol. 2, No. 1: 114-128 (Feb. 2012).
Araujo, R. et al., "Unpredictable susceptibility of emerging clinical moulds to tri-azoles: review of the literature and upcoming challenges for mould identification," European Journal of Microbiology, 34: 1289-1301, 2015.
Cortez, K. J. et al., "Infections Caused by *Scedosporium spp.*", Clinical Microbiology Reviews, 21(1): 157-197, 2008.
Milhazes, N. et al., "β-Nitrostyrene derivatives as potential antibacterial agents: A structure-property-activity relationship study," Bioorganic and Medicinal Chemistry, 14: 4078-4088, 2006.
Nicoletti, G. et al., "Synthesis and Antimicrobial Activity of Nitroalkenyl Arenes," Anti-Infective Agents, 11: 179-191, 2013.
Pettit, R. K. et al., "E-Combretastatin and E-resveratrol structural modifications: Antimicrobial and cancer cell growth inhibitory β-E-nitrostyrenes," Bioorganic and Medicinal Chemistry, 17: 6606-6612, 2009.
Reinoso, R. et al., "Fatal disseminated *Scedosporium prolificans* infection initiated by ophthalmic involvement in a patient with acute myeloblastic leukemia," Diagnostic Microbiology and Infectious Disease, 76: 375-378, 2013.
Rodriguez-Tudela, J. L. et al., "Epidemiology and outcome of *Scedosporium prolificans* infection, a review of 162 cases," Medical Mycology, 47: 359-370, 2009.
Supplementary European Search Report for EP 13798071 dated Sep. 17, 2015.

* cited by examiner

*Primary Examiner* — Fred H Reynolds
(74) *Attorney, Agent, or Firm* — McCarter & English, LLP; Maria Laccotripe Zacharakis; Wei Song

(57) ABSTRACT

The present invention provides a method of treatment of *Scedosporium* spp. infection in an animal comprising the step of administering to the infected animal an effective amount of a compound of formula I or a pharmaceutically-acceptable salt thereof.

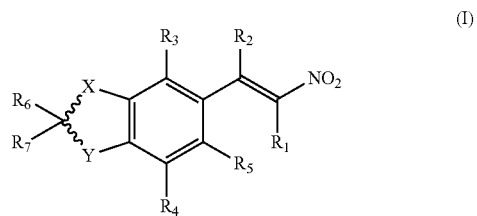

4 Claims, No Drawings

METHOD OF TREATING *SCEDOSPORIUM* SPP. INFECTION

RELATED APPLICATIONS

The present application is a 35 U.S.C. 371 national stage filing of International Application No. PCT/AU2013/000487, filed on 13 May 2013, which claims priority to Australian provisional patent application no. 2012902243 filed on 30 May 2012, the entire contents of each of which are incorporated herein by reference.

FIELD OF THE INVENTION

This invention relates to a method of treating *Scedosporium* spp. infection in animals, in particular humans. The method involves the use of certain substituted nitrostyrene compounds.

BACKGROUND OF THE INVENTION

The genus *Scedosporium* consists of two medically important species: *Scedosporium apiospermum* (and its teleomorph or sexual state *Pseudallescheria boydii*) and *Scedosporium prolificans* (formerly *S. inflatum*). *S. apiospermum/P. boydii* and *S. prolificans* are ubiquitous filamentous fungi present in soil, sewage, and polluted waters. Scedosporiosis represents a broad spectrum of clinical diseases caused by the agents of the genus *Scedosporium*. These fungi can be colonizers of previously damaged bronchopulmonary trees (as in old pulmonary tuberculosis cases, cystic fibrosis, or bronchiectatic lungs of any etiology). Infections caused by these organisms can be localized, extend to the surrounding tissues (deep extension), or disseminate (hematogenously) to distant organs. The range of diseases caused by these fungi is broad, ranging from transient colonization of the respiratory tract to saprophytic involvement of abnormal airways, allergic bronchopulmonary reaction, invasive localized disease, and at times disseminated disease. These infections include skin and soft tissue infections with extension to tendons, ligaments, and bone (mycetoma); septic arthritis; osteomyelitis; lymphocutaneous syndrome; pneumonia; endocarditis; peritonitis; meningoencephalitis; meningitis; brain abscess; parotitis; thyroid abscess; otomycosis; sinusitis; keratitis; chorioretinitis; and endophthalmitis. The disseminated form of the disease is mostly seen among immunocompromised patients; however, even in immunocompetent individuals, cases of disseminated disease have been reported.

*Scedosporium* spp. are increasingly recognized as causes of resistant life-threatening infections in immunocompromised patients. *Scedosporium* spp. also cause a wide spectrum of conditions, including mycetoma, saprobic involvement and colonization of the airways, sinopulmonary infections, extrapulmonary localized infections, and disseminated infections. Invasive *scedosporium* infections are also associated with central nervous infection following near-drowning accidents. The most common sites of infection are the lungs, sinuses, bones, joints, eyes, and brain. *Scedosporium apiospermum* and *Scedosporium prolificans* are the two principal medically important species of this genus. *Pseudallescheria boydii*, the teleomorph of *S. apiospermum*, is recognized by the presence of cleistothecia. Recent advances in molecular taxonomy have advanced the understanding of the genus *Scedosporium* and have demonstrated a wider range of species than heretofore recognized.

Studies of the pathogenesis of and immune response to *Scedosporium* spp. underscore the importance of innate host defenses in protection against these organisms. Infections caused by *S. apiospermum* and *P. boydii* in patients and animals may respond to antifungal triazoles. By comparison, infections caused by *S. prolificans* seldom respond to medical therapy alone. Surgery and reversal of immunosuppression may be the only effective therapeutic options for infections caused by *S. prolificans*.

WO 02/102789, the disclosure of which is incorporated herein by reference, discloses a number of substituted nitrostyrene compounds that have anti-microbial activity against a range of microorganism. The present inventors have now surprisingly found that certain of these substituted nitrostyrene compounds have excellent activity against *Scedosporium* spp.

SUMMARY OF THE INVENTION

The present invention provides a method of treatment of *Scedosporium* spp. infection in an animal comprising the step of administering to the infected animal an effective amount of a compound of formula I or a pharmaceutically-acceptable salt thereof

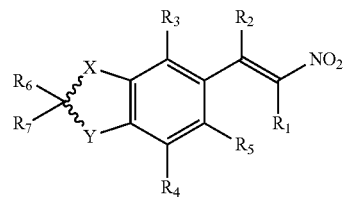

in which

X and Y are either the same or different and are each a heteroatom selected from the group consisting of O, N, and S;

⌇ is a double or single bond depending on the heteroatoms X and Y;

$R_1$ to $R_5$ are either the same or different and selected from hydrogen, alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, alkylthio, arylthio, acylthio or phosphorus-containing compounds; and $R_6$ and $R_7$ are either the same or different, and selected from hydrogen, alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, alkylthio, arylthio, acylthio or phosphorus-containing compounds, or one of $R_6$ and $R_7$ are absent when there is a double bond present.

The invention further provides use of the compound of formula I, or a pharmaceutically-acceptable salt thereof, for the treatment of *Scedosporium* spp. infection.

The invention also provides the use of the compound of formula I, or a pharmaceutically-acceptable salt thereof, in the preparation of a medicament for treatment of *Scedosporium* spp. infection.

Preferably X and Y are either the same or different and selected from O and N, more preferably both X and Y are oxygen.

Preferably R1 and R2 are either the same or different and selected from hydrogen, hydroxy, halogen or optionally substituted C1-6 alkyl.

$R_3$ to $R_5$ are preferably either the same or different and selected from hydrogen, hydroxy, halogen, nitro, $C_{1-6}$ alkoxy or optionally substituted $C_{1-6}$ alkyl. Preferably halogen is chlorine or bromine.

The E isomer of the compounds of formula I is preferred.

Particularly preferred are compounds of the formula I in which X, Y, $R_6$ and $R_7$ are as defined above; $R_1$ and $R_2$ are either the same or different and selected from hydrogen, hydroxy, Cl, Br and $C_{1-4}$ alkyl; and $R_3$ to $R_5$ are either the same or different and selected from hydrogen, hydroxy, Cl, Br, nitro, $C_{1-4}$ alkoxy or $C_{1-4}$ alkyl.

Specific examples of the compounds of the present invention are as follows:

(1) X and Y are 0, $R_1$ is methyl and $R_2$ and $R_3$ are hydrogen (3,4-methylenedioxy-β-methyl-β-nitrostyrene)

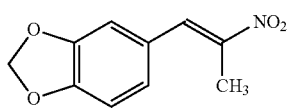

(2) X and Y are 0 and $R_1$ to $R_3$ are hydrogen (3,4-methylenedioxy-β-nitrostyrene)

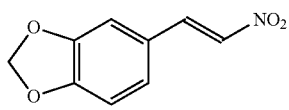 [SMILES: O=[N+]([O-])/C=C/c1ccc2c(c1)OCO2]

(3) X is N, Y is NH, $R_1$ is methyl and $R_2$ and $R_3$ are hydrogen (benzimidazole-5-β-nitropropylene)

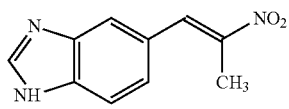

(4) X is N, Y is NH, $R_1$ is hydrogen, $R_2$ is methyl and $R_3$ is absent (2-methyl benzimidazole-5-β-nitroethylene)

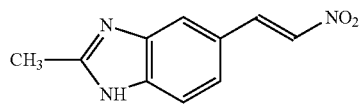

(5) X is O, Y is N, $R_1$ and $R_2$ are hydrogen and $R_3$ is absent (benzoxazole-5-β-nitroethylene)

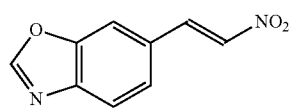 [SMILES: O=[N+]([O-])/C=C/c1ccc2ncoc2c1]

(6) X is N, Y is O, $R_1$ and $R_2$ are methyl and $R_3$ is absent (2-methyl benzoxazole-5-β-nitropropylene)

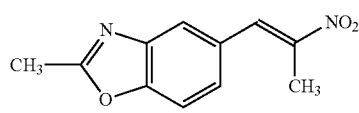

In a further aspect, the invention provides a pharmaceutical or veterinary composition comprising the compound of formula I defined above together with a pharmaceutically or veterinarily acceptable carrier. Preferably, the pharmaceutical or veterinary composition is a topical, oral or parenteral composition.

The pharmaceutically or veterinarily acceptable carrier is preferably an organic solvent such as acetone, benzene, acetonitrile, DMSO or an alcohol, for example, methanol or ethanol. While the compounds of the present invention show a poor solubility in water, when water is combined with an organic solvent a stable mixture is formed.

DETAILED DESCRIPTION OF THE INVENTION

For the purposes of this specification it will be clearly understood that the word "comprising" means "including but not limited to", and that the word "comprises" has a corresponding meaning.

The term "heteroatom" denotes O, N or S.

The term "halogen" refers to fluorine, chlorine, bromine and iodine, preferably chlorine and bromine.

The term "alkoxy" is used herein in its broadest sense and refers to straight chain, branched chain or cyclic oxy-containing radicals each having alkyl portions, preferably $C_{1-6}$ alkyl, more preferably $C_{1-4}$ alkyl. Examples of such alkoxy groups are methoxy, ethoxy, propoxy, butoxy and t-butoxy.

The terms "$C_{1-4}$ alkyl" or "$C_{1-6}$ alkyl" refer to straight chain, branched chain or cyclic hydrocarbon groups having from 1 to 6 carbon atoms. Illustrative of such alkyl groups are methyl, ethyl, propyl, isopropyl, butyl, isobutyl, sec-butyl, tert-butyl, pentyl, neopentyl, hexyl, cyclopropyl, cyclobutyl, cyclopentyl or cyclohexyl.

The salts of the compound of formula I are preferably pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

In addition, some of the compounds of the present invention may form solvates with water or common organic solvents. Such solvates are encompassed within, the scope of the invention.

By "pharmaceutically acceptable derivative" is meant any pharmaceutically acceptable salt, hydrate or any other compound which, upon administration to the subject, is capable of providing (directly or indirectly) a compound of formula I or active metabolite or residue thereof.

The term "pro-drug" is used herein in its broadest sense to include those compounds which are converted in vivo to compounds of formula I.

The term "tautomer" is used herein in its broadest sense to include compounds of formula I which are capable of existing in a state of equilibrium between two isomeric forms. Such compounds may differ in the bond connecting two atoms or groups and the position of these atoms or groups in the compound.

The term "isomer" is used herein in its broadest sense and includes structural, geometric and stereo isomers. As the compound of formula I or Ia may have one or more chiral centres, it is capable of existing in enantiomeric forms.

The term "subject" as used herein refers to any animal having a disease or condition which requires treatment with a pharmaceutically-active agent. The subject may be a mammal, preferably a human, or may be a domestic or companion animal. While it is particularly contemplated that the compounds of the invention are suitable for use in medical treatment of humans, it is also applicable to veterinary treatment, including treatment of companion animals such as dogs and cats, and domestic animals such as horses, ponies, donkeys, mules, llama, alpaca, pigs, cattle and sheep, or zoo animals such as primates, felids, canids, bovids, and ungulates.

As used herein, the term "effective amount" is meant an amount of a compound of Formula I effective to yield a desired activity against the *Scedosporium* spp. infection.

The specific "effective amount" will, obviously, vary with such factors as the particular condition being treated, the physical condition of the subject, the type of subject being treated, the duration of the treatment, the nature of concurrent therapy (if any), and the specific formulations employed and the structure of the compound or its derivatives.

The compounds of the present invention may additionally be combined with one or more other medicaments to provide an operative combination. It is intended to include any chemically compatible combination of pharmaceutically-active agents, as long as the combination does not eliminate the activity of the compound of formula I. It will be appreciated that the compound of the invention and the other medicament may be administered separately, sequentially or simultaneously.

Other medicaments which may be used when treating microbial infections include other anti-infective agents such as antibiotics. It is preferred that the other medicament is selected from the group consisting of amphotericin B, fluconazole, itraconazole, ketoconazole, voriconazole, terbinafine and other allylamines, griseofulvin, benzoic acid, ciclopirox, 5-flucytosine, undecyenic acid, crystal violet, tolnaftate, nystatin, clotrimazole and other imidazoles, amorolfine, caspofungin and other echinocandins, and combinations thereof.

As used herein, a "pharmaceutical carrier" is a pharmaceutically acceptable solvent, suspending agent or vehicle for delivering the compound of formula I to the subject: The carrier may be liquid or solid and is selected with the planned manner of administration in mind. Each carrier must be pharmaceutically "acceptable" in the sense of being compatible with other ingredients of the composition and non injurious to the subject.

The compound of formula I may be administered orally, topically, parenterally transdermally, by inhalation, intranasally, by irrigation, by implant, by insufflation, topically to the eye, or aurally. The compound may be administered to body cavities including ear, sinuses, and bladder. The compound may be administered in dosage unit and in formulations containing conventional non-toxic pharmaceutically acceptable carriers, adjuvants, and vehicles. Formulations include liposomal, nanoparticle, microparticle, polymer-based, dispersion, suspension, coated on a device, powder, microspheres, carrier-mediated, implant and encapsulation. The term parenteral as used herein includes subcutaneous injections, aerosol for administration to lungs or nasal cavity, intravenous, intramuscular, intrathecal, intracranial, injection or infusion techniques. The present invention also provides suitable topical, oral and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. Suitable sweeteners include sucrose, lactose, glucose, aspartame or saccharin. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable preservatives include sodium benzoate, vitamin E, alphatocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate. The tablets contain the active ingredient in admixture with non-toxic pharmaceutically acceptable excipients which are suitable for the manufacture of tablets. These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

The compound of formula I can be administered, for in vivo application, parenterally by injection or by gradual perfusion over time independently or together. Administration may be intravenously, intraarterial, intraperitoneally, intramuscularly, subcutaneously, intracavity, transdermally or infusion by, for example, osmotic pump.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, growth factors and inert gases and the like.

Generally, the terms "treating", "treatment" and the like are used herein to mean affecting a subject, tissue or cell to obtain a desired pharmacologic and/or physiologic effect. The effect may be prophylactic in terms of completely or partially preventing a disease or sign or symptom thereof, and/or may be therapeutic in terms of partial or complete cure of the infection or amelioration of at least one symptom of the infection.

The pharmaceutical compositions according to one embodiment of the invention are prepared by bringing a compound of formula I, analogues, derivatives or salts thereof, or combinations of compound of formula I and one or more pharmaceutically-active agents into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 20th ed. Williams & Williams (2000), the British National Formulary, 43$^{rd}$ edition (British Medical Association and Royal Pharmaceutical Society of Great Britain, 2000), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed., 1985).

The pharmaceutical compositions are preferably prepared and administered in dose units. Solid dose units may be tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Various considerations are described, e.g., in Langer, Science, 249: 1527, (1990). Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil. Aqueous suspensions normally contain the active materials in admixture with excipients suitable for the manufacture of aqueous suspension. Such excipients may be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables. The compound of formula I may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compound of formula I may also be presented for use in the form of veterinary compositions, which may be prepared, for example, by methods that are conventional in the art. Examples of such veterinary compositions include those adapted for: (a) oral administration, external application, for example drenches (e.g. aqueous or non-aqueous solutions or suspensions); tablets or boluses; powders, granules or pellets for admixture with feed stuffs; pastes for application to the tongue; (b) parenteral administration for example by subcutaneous, intramuscular or intravenous injection, e.g. as a sterile solution or suspension; or (when appropriate) by intramammary injection where a suspension or solution is introduced in the udder via the teat; (c) topical applications, e.g. as a cream, ointment or spray applied to the skin; or (d) intravaginally, e.g. as a pessary, cream or foam.

Dosage levels of the compound of formula I of the present invention may be of the order of up to about 1 gram per kilogram body weight. The amount of active ingredient that may be combined with the carrier materials to produce a single dosage will vary depending upon the host treated and the particular mode of administration. For example, a formulation intended for oral administration to humans may contain up to about 1 gram of an active compound with an appropriate and convenient amount of carrier material which may vary from about 5 to about 95 percent of the total composition. Dosage unit forms will generally contain between from about 5 mg to about 500 mg of active ingredient.

Optionally the compounds of the invention are administered in a divided dose schedule, such that there are at least two administrations in total in the schedule. Administrations are given preferably at least every two hours for up to four hours or longer; for example the compound may be administered every hour or every half hour. In one preferred embodiment, the divided-dose regimen comprises a second administration of the compound of the invention after an interval from the first administration sufficiently long that the level of active compound in the blood has decreased to approximately from 5-30% of the maximum plasma level reached after the first administration, so as to maintain an effective content of active agent in the blood. Optionally one or more subsequent administrations may be given at a corresponding interval from each preceding administration, preferably when the plasma level has decreased to approximately from 1.0-50% of the immediately-preceding maximum. It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLES

The invention will now be described in detail by way of reference only to the following non-limiting examples.

Example 1 General Synthesis Methods

Benzdioxols are described in the literature (Perekalkin, 1982a). The synthesis of benzoimidazole and benzoxazole may also be carried out using standard condensation methods 1 and 2 (Perekalkin, 1966, 1982b) as shown below.

Method 1

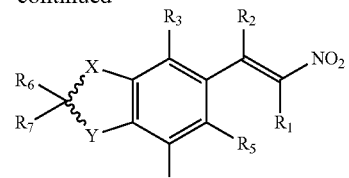

-continued

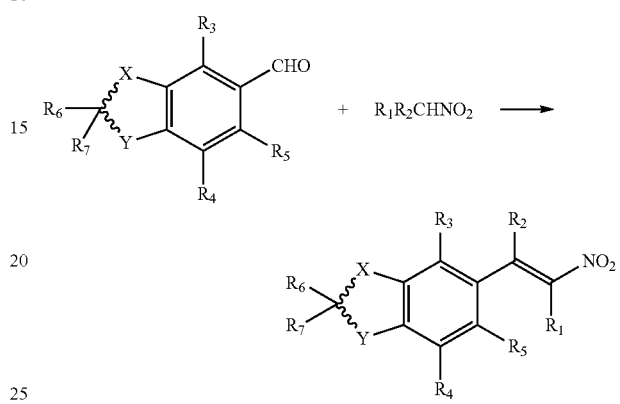

Method 2 in which X, Y, $\xi$ and $R_x$ to $R_7$ are as defined in Formula I above.

In Method 2, equimolecular quantities of benzaldehyde and nitroalkane were mixed in an Erlenmayer flask and dissolved in equal volume of alcohol. Fresh distilled ethylenediamine was added to the obtained solution in catalytical quantities (usually 1:10 in relation to aldehyde and nitroalkane) and was left in the dark at room temperature for several days (from 3 up to 10 days). During this time the compound crystallised. After the cooling up to about 0° C., the crystals were filtrated and washed with cold alcohol and then dried. When the yield is small, the mother liquids can be joined together and evaporated in rotary evaporator. After cooling the additional quantity of impure product is obtained. The product was purified by dissolving in a minimal quantity of boiling alcohol. It was then treated with activated carbon, filtered hot and while the cooling was in progress, fine yellow needles crystallised. The yield was about 80-85%, the compound being chromatographically homogeneous.

The infrared spectra of the compounds obtained are in accordance with those described in the literature (Hamlin and Weston, 1949; Knoevenagel and Walter, 1904; Burton and Duffield, 1949).

The compounds were soluble in organic solvents such as ethanol, acetone, benzene, methanol, acetonitrile, chloroform and DMSO, but showed very poor solubility in water (0.1%). When an alcoholic solution was added to water, a stable colloidal mixture was formed.

Example 2 Method for Preparing Compound (1) (3,4-methylenedioxy-β-methyl-β-nitrostyrene)

Compound (1) was prepared using Method 1 described in Example 1 above. The reaction scheme is shown below.

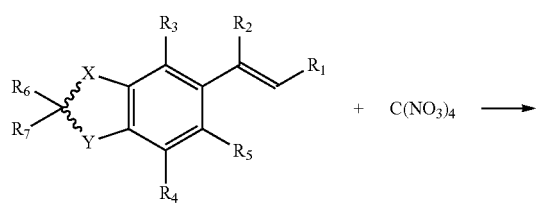

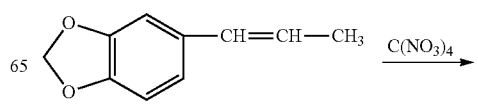

-continued

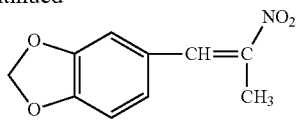

A mixture of 9.8 g of tetranitromethane (I mole) and 10 cm³ of acetone was cooled by ice and added dropwise to 8.1 g of distilled isosafrole (I mole) and 4.8 g of pyridine (1.2 mole) dissolved in 20 cm³ of acetone. The very first drops caused darkening of the reaction mixture and the liquid turned non-transparent and murky red when the entire portion of tetranitromethane was added. The smell of tetranitromethane disappeared quickly and in approximately 2 hours the dark red solution which had turned transparent was poured into 100 cm³ of water in a stoppered bottle. The mixture was thoroughly shaken, covered with a layer of ether and a mixture of 6.7 cm³ of 33% solution of caustic potassium (1.03 mole) and 50 cm³ of water was added in small portions. The mixture was shaken after each addition and once the entire amount of alkali was added, the shaking was continued until the entire salt of pyridine and nitroform, which is present as a dark red oil, disappeared. The water layer was then separated and again extracted with ether. Combined ether extracts were first rinsed with water and then with water acidified with sulphuric acid and finally once again with pure water. After distillation of the ether in the vacuum, a sediment of β-nitroisosafrole was to be found in the form of yellow needles, which were re-crystallized from approximately 65 cm³ of alcohol. Compound (1) was obtained with a melting point of 98° C. and a yield of 7 g. Once the solvent had evaporated, another 0.5 g of Compound (1) was obtained. The total product amounted to 72.5% of the theoretical yield.

Example 3 Alternative Method for Preparing Compound (1) (3,4-methylenedioxy-β-methyl-β-nitrostyrene)

Compound (1) was prepared using Method 2 described in Example 1 above. The reaction scheme is shown below.

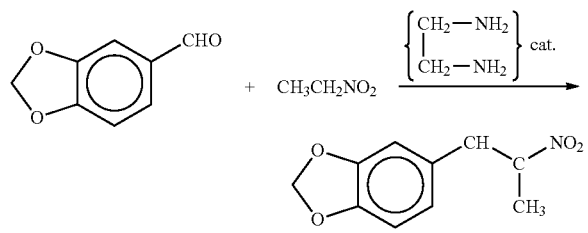

900 gm piperonal was dissolved in 1000 cc alcohol with constant shaking and 450 ml nitroethane was added slowly followed by 10 ml ethyldiamine. After 17 hrs stirring, the mixture was placed in the dark at room temperature for 5-7 days. The resulting yellow crystals were filtrated in a Buchner funnel until dried and then washed twice with 150 ml alcohol. This yielded 1200 gm of Compound (1) with melting point of 95° C. After further crystallization from ethanol, 1000 gm of light yellow crystals were obtained with a melting point of 98° C. (approx 80% yield).

Molecular formula $C_{10}H_9NO_4$, molecular weight—207.05

Physical and Chemical Characteristics

| Form of state | yellow crystals |
|---|---|
| Solubility profile | soluble in ethanol, acetone, benzene, methanol, acetonitrile, chloroform, DMSO almost insoluble in water |
| Melting point | 94-98° C. (when crystallized from 50% ethanol product had 96-98° C.) |
| pH (in 50% v/v ethanol) | approximately neutral |
| Specific rotation | optically inactive but has 2 stereoisomers |
| Stability | begins to darken above 200° C. |
| Purity | MS indicates impurities of molecular weight 303.4 & 331.4 to be the major impurities |

Example 4 Process for Preparing Compound (2)

Compound (2) was prepared using Method 2 described in Example 1 above. The reaction scheme is shown below.

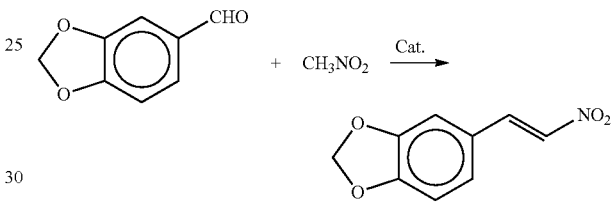

3,4-methylenedioxybenzaldehyde was condensed with nitromethane using fresh distillated ethylenediamine $NH_2$—$CH_2$—$CH_2$—$NH_2$ as a catalyst. The reaction was conducted in alcohol, darkness and at room temperature for 5 days. The resultant crystals were separated by filtration and washed with cold alcohol. After being dried in air, the yield was 80%, m.p.—158-159° C. and after re-crystallization the m.p. was 162-163° C. Compound (2) was non-soluble in water, soluble in acetone, alcohol, acetic acid and in a majority of organic solvents.

Example 5 In Vitro Activity of Compound (1) Against *Scedosporium* Spp.

In vitro susceptibility to Compound (1) was assessed against *Scedosporium* spp. A stock solution of 1 mg/ml of Compound (1) was made in 100% DMSO. The stock was aliquoted and stored at −80° C.

Three strains *Scedosporium prolificans* and 3 strains of *S. apiospermum/P. boydii* were tested. Each isolate was tested in duplicate and on two separate occasions. The results are set out in Table 1.

TABLE 1

| Strain | Arithmetic Mean MIC (mg/L) of 4 readings |
|---|---|
| *S. prolificans* MB 10028425 | 2 |
| *S. prolificans* 04-11-1472398 | 2 |
| *S. prolificans* (Austin Pathology) | 1 |
| *S. apsiopermum* 04-10-2013595 | 2 |
| *S. apiospermum* 04-10-1932310 | 4 |
| *P. boydii* 01-10-1391979 | 4 |

Compound (1) appears to be most active against *S. prolificans* which is unexpected as this species is resistant to most azoles and AMB.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Burton, H., Duffield, G., J. Chem. Soc., 1949, 78

Denisenko P. P., Tarasenko A. A., Russian patent No. 2145215, "Substances having antimicrobial, antifungal, antiprotozoal activity" published 10 Feb. 2000

Foyer, G., Chemistry of nitro and nitroso groups, Moscow, 1973, Pt. 2, pp. 194-195

Garcia, L., Parasite culture: *Trichomonas vaginalis*, Clinical Microbiology Procedures Handbook, H. D. Isenberg (ed.), volume 2, American Society for Microbiology, Washington, USA, 7.9.3.1-7.9.3.6.

Hamlin, K. Weston, A., J. Am. Chem. Soc. 71, 2210 (1949)

Knoevenagel, E., Walter, L., Ber 37, 4502 (1904)

Kuna P., Chemical radiation protection, Moscow, 1989, pp. 25-28

Mashkovskiy M. D., Clinical agents, Pt. 2, Moscow, 1986, p. 189

Perekalkin V. V., Unlimited nitrocompounds, Leningrad, 1982, pp. 55, 59, 61, 71, 73, 88, 89, 91, 95

Perekalkin V. V., Unlimited nitrocompounds, Leningrad, 1982, p. 67

Perekalkin V. V., Unlimited nitrocompounds, Moscow, 1966, p. 119

Vladimirov V. G. et al., Radiation protectors, structure and operation, Kiev, 1989, p. 139

The invention claimed is:

1. A method for treatment of *Scedosporium prolificans* infection in an animal, the method comprising administering to the infected animal an effective amount of the compound 3,4-methylenedioxy-β-methyl-β-nitrostyrene.

2. The method of claim 1, wherein the compound 3,4-methylenedioxy-β-methyl-β-nitrostyrene is administered in combination with at least one other compound selected from the group consisting of amphotericin B, fluconazole, itraconazole, ketoconazole, voriconazole, terbinafine and other allylamines, griseofulvin, benzoic acid, ciclopirox, 5-flucytosine, undecyenic acid, crystal violet, tolnaftate, nystatin, clotrimazole and other imidazoles, amorolfine, and caspofungin and other echinocandins.

3. The method of claim 1, wherein the animal is a human.

4. The method of claim 1 wherein the *Scedosporium* spp. infection is infection of a site selected from the group consisting of lungs, sinuses, bones, joints, eyes, and brain.

* * * * *